US011286172B2

(12) United States Patent
Russell, II et al.

(10) Patent No.: US 11,286,172 B2
(45) Date of Patent: *Mar. 29, 2022

(54) METAL-MOLYBDATE AND METHOD FOR MAKING THE SAME

(71) Applicant: BWXT Isotope Technology Group, Inc., Lynchburg, VA (US)

(72) Inventors: William Earl Russell, II, Lynchburg, VA (US); Earl Brian Barger, Goode, VA (US); Benjamin I. Bishop, Charlotte, NC (US); Barbara B. Bohannon, Charlotte, NC (US); Christopher Sean Fewox, Forest, VA (US); James B. Inman, Forest, VA (US); Erik T. Nygaard, Lynchburg, VA (US); Timothy A. Policke, Forest, VA (US); Stephen D. Preite, Charlotte, NC (US); Roger D. Ridgeway, Rustburg, VA (US); Steve W. Schilthelm, Lynchburg, VA (US); Bryan Blake Wiggins, Forest, VA (US)

(73) Assignee: BWXT Isotope Technology Group, Inc., Lynchburg, VA (US)

( * ) Notice: Subject to any disclaimer, the term of this patent is extended or adjusted under 35 U.S.C. 154(b) by 583 days.

This patent is subject to a terminal disclaimer.

(21) Appl. No.: 15/902,140

(22) Filed: Feb. 22, 2018

(65) Prior Publication Data

US 2018/0244536 A1    Aug. 30, 2018

Related U.S. Application Data

(60) Provisional application No. 62/592,737, filed on Nov. 30, 2017, provisional application No. 62/463,020, filed on Feb. 24, 2017.

(51) Int. Cl.
*C01G 39/00* (2006.01)
*A61K 51/02* (2006.01)

(52) U.S. Cl.
CPC .......... *C01G 39/006* (2013.01); *A61K 51/025* (2013.01); *C01G 39/00* (2013.01);
(Continued)

(58) Field of Classification Search
CPC ..... C01G 39/006; C01G 39/00; A61K 51/025
See application file for complete search history.

(56) References Cited

U.S. PATENT DOCUMENTS 3,140,393 A    7/1964  Busch
3,436,354 A *  4/1969  Molinski ................ A61K 51/04
                                                    424/1.61
(Continued)

FOREIGN PATENT DOCUMENTS

AR    009481 A1    4/2000
AR    019754 A1    3/2002
(Continued)

OTHER PUBLICATIONS

Scadden et al ("Radiochemistry of Molybdenum", National Academy of Sciences, 1960, pp. 1-38). (Year: 1960).*
(Continued)

*Primary Examiner* — Sheng H Davis
*Assistant Examiner* — Michael Forrest
(74) *Attorney, Agent, or Firm* — Nelson Mullins Riley & Scarborough LLP

(57) ABSTRACT

A process for producing a metal-molybdate material is provided. The process includes a step of reacting a metal molybdenum (Mo) material in a liquid medium with a first acid to provide a Mo composition and combining the Mo composition with a metal source to provide a metal-Mo composition. The metal-Mo composition can be pH adjusted (Continued)

with a base to precipitate a plurality of metal-Mo particulates.

60 Claims, 5 Drawing Sheets

(52) U.S. Cl.
CPC ...... *C01P 2004/60* (2013.01); *C01P 2004/61* (2013.01); *C01P 2006/44* (2013.01)

(56) References Cited

U.S. PATENT DOCUMENTS

| | | | |
|---|---|---|---|
| 3,607,007 A * | 9/1971 | Chiola | C22B 34/30 423/54 |
| 3,666,822 A * | 5/1972 | Grasselli | B01J 37/0201 585/626 |
| 3,752,769 A | 8/1973 | Lewis et al. | |
| 4,123,497 A | 10/1978 | Ruddock | |
| 4,141,861 A * | 2/1979 | Courty | B01J 23/8871 502/302 |
| 4,273,745 A | 6/1981 | Laferty et al. | |
| 4,280,053 A * | 7/1981 | Evans | G21G 1/04 250/432 PD |
| 4,360,495 A | 11/1982 | Bauer | |
| 4,440,729 A * | 4/1984 | Jonsson | H01K 3/02 216/93 |
| 4,487,850 A | 12/1984 | Li | |
| 4,525,331 A | 6/1985 | Cheresnowsky et al. | |
| 4,738,834 A | 4/1988 | Moore et al. | |
| 4,756,746 A | 7/1988 | Kemp, Jr. et al. | |
| 4,760,638 A | 8/1988 | Ott et al. | |
| 4,782,231 A | 11/1988 | Svoboda et al. | |
| 5,382,388 A | 1/1995 | Ehrhardt et al. | |
| 5,397,902 A | 3/1995 | Castner et al. | |
| 5,615,238 A | 3/1997 | Wiencek et al. | |
| 5,802,438 A * | 9/1998 | Bennett | G21G 1/12 376/186 |
| 5,821,186 A | 10/1998 | Collins | |
| 5,846,455 A | 12/1998 | David et al. | |
| 6,103,295 A | 8/2000 | Chan et al. | |
| 6,113,795 A | 9/2000 | Subramaniam et al. | |
| 6,136,740 A * | 10/2000 | Jones | B01J 20/12 501/144 |
| 6,160,862 A | 12/2000 | Wiencek et al. | |
| 6,166,284 A | 12/2000 | Oelsner | |
| 6,394,945 B1 | 5/2002 | Chan et al. | |
| 6,638,205 B1 | 10/2003 | Chan et al. | |
| 6,676,988 B2 | 1/2004 | Chan et al. | |
| 6,793,798 B2 | 9/2004 | Chan et al. | |
| 8,270,555 B2 | 9/2012 | Hannah et al. | |
| 8,318,113 B2 | 11/2012 | Barbosa | |
| 8,437,443 B2 | 5/2013 | Russell, II et al. | |
| 8,488,733 B2 | 7/2013 | Allen et al. | |
| 8,542,789 B2 | 9/2013 | Russell, II et al. | |
| 8,569,713 B2 | 10/2013 | Evers | |
| 8,638,899 B2 | 1/2014 | Smith et al. | |
| 8,699,651 B2 | 4/2014 | Bloomquist et al. | |
| 8,753,590 B2 | 6/2014 | Barbosa | |
| 8,781,055 B2 | 7/2014 | Toth et al. | |
| 8,822,950 B2 | 9/2014 | Evers | |
| 8,842,798 B2 | 9/2014 | Russell et al. | |
| 8,872,124 B2 | 10/2014 | Graves et al. | |
| 8,900,340 B2 | 12/2014 | Abenthung et al. | |
| 8,911,695 B2 | 12/2014 | Hasan | |
| 8,932,091 B2 | 1/2015 | Nicholson et al. | |
| 8,953,731 B2 | 2/2015 | Fawcett et al. | |
| 8,989,335 B2 | 3/2015 | Tsang | |
| 9,047,997 B2 | 6/2015 | Tsang | |
| 9,076,561 B2 | 7/2015 | Brown | |
| 9,183,959 B2 | 11/2015 | Bloomquist et al. | |
| 9,239,385 B2 | 1/2016 | Fawcett et al. | |
| 9,240,253 B2 | 1/2016 | Varnedoe et al. | |
| 9,285,487 B2 | 3/2016 | Graves et al. | |
| 9,362,009 B2 | 6/2016 | Russell, II et al. | |
| 9,396,825 B2 | 7/2016 | Bloomquist et al. | |
| 9,443,629 B2 | 9/2016 | Tsang | |
| 9,550,704 B2 | 1/2017 | Chi et al. | |
| 9,576,691 B2 | 2/2017 | Tsang | |
| 9,587,292 B2 | 3/2017 | Lapi et al. | |
| 10,820,404 B2 | 10/2020 | Cross et al. | |
| 2005/0063514 A1 | 3/2005 | Price et al. | |
| 2005/0156144 A1 * | 7/2005 | Fukushima | B82Y 30/00 252/500 |
| 2006/0144793 A1 | 7/2006 | Dadachov | |
| 2007/0086909 A1 | 4/2007 | Abenthung et al. | |
| 2007/0133731 A1 | 6/2007 | Fawcett et al. | |
| 2007/0155976 A1 | 7/2007 | Hunter et al. | |
| 2008/0006606 A1 | 1/2008 | Magnaldo | |
| 2009/0135990 A1 | 5/2009 | Poon et al. | |
| 2009/0274258 A1 | 11/2009 | Holden et al. | |
| 2010/0266083 A1 | 10/2010 | Bloomquist et al. | |
| 2011/0006186 A1 | 1/2011 | Allen et al. | |
| 2011/0009686 A1 | 1/2011 | Allen et al. | |
| 2011/0051872 A1 | 3/2011 | Rickard et al. | |
| 2011/0051875 A1 | 3/2011 | Bloomquist et al. | |
| 2011/0079108 A1 | 4/2011 | Lapi et al. | |
| 2011/0096887 A1 | 4/2011 | Piefer | |
| 2011/0250107 A1 | 10/2011 | Varnedoe et al. | |
| 2011/0280356 A1 | 11/2011 | Tsang | |
| 2011/0286565 A1 | 11/2011 | Tsang | |
| 2012/0027152 A1 | 2/2012 | Reese et al. | |
| 2012/0073958 A1 | 3/2012 | Abenthung et al. | |
| 2012/0285294 A1 | 11/2012 | Shanks et al. | |
| 2013/0039822 A1 | 2/2013 | Hasan | |
| 2013/0136221 A1 | 5/2013 | Nishikata et al. | |
| 2013/0220928 A1 | 8/2013 | Oelsner | |
| 2013/0301769 A1 | 11/2013 | Schaffer et al. | |
| 2013/0312570 A1 | 11/2013 | Barbosa | |
| 2013/0336436 A1 | 12/2013 | Allen et al. | |
| 2014/0029710 A1 | 1/2014 | Wilson et al. | |
| 2014/0133617 A1 | 5/2014 | Bloomquist et al. | |
| 2014/0140462 A1 | 5/2014 | Barbosa | |
| 2014/0192942 A1 | 7/2014 | Tsechanski | |
| 2014/0231709 A1 | 8/2014 | Barbosa | |
| 2014/0234186 A1 | 8/2014 | Barbosa | |
| 2015/0023876 A1 | 1/2015 | Cope et al. | |
| 2015/0139870 A1 | 5/2015 | Hasan | |
| 2015/0243395 A1 | 8/2015 | Tsang | |
| 2015/0243396 A1 | 8/2015 | Tsang | |
| 2016/0023182 A1 | 1/2016 | Tadokoro et al. | |
| 2016/0141061 A1 | 5/2016 | Burgett | |
| 2016/0148712 A1 | 5/2016 | Sandquist | |
| 2017/0032860 A1 | 2/2017 | Tsang | |
| 2017/0048962 A1 | 2/2017 | Zeisler et al. | |
| 2017/0251547 A1 | 8/2017 | Ito | |
| 2018/0244535 A1 | 8/2018 | Russell, II et al. | |
| 2018/0244536 A1 | 8/2018 | Russell, II et al. | |

FOREIGN PATENT DOCUMENTS

| | | |
|---|---|---|
| AR | 077648 A1 | 9/2011 |
| AR | 102621 A1 | 3/2017 |
| AR | 104305 A1 | 7/2017 |
| AR | 104411 A1 | 7/2017 |
| AR | 105386 A1 | 9/2017 |
| CA | 2321183 A1 | 10/1999 |
| CA | 2506391 A1 | 11/2005 |
| CA | 2643841 A1 | 5/2009 |
| CA | 2653871 A1 | 8/2009 |
| CA | 2723224 A1 | 11/2009 |
| CA | 2724024 A1 | 11/2009 |
| CA | 2698773 A1 | 10/2010 |
| CA | 2767395 A1 | 1/2011 |
| CA | 2713237 A1 | 2/2011 |
| CA | 2933961 A1 | 8/2011 |
| CA | 2735612 A1 | 10/2011 |
| CA | 2806584 A1 | 2/2012 |
| CA | 2816648 A1 | 5/2012 |
| CA | 2832750 A1 | 10/2012 |
| CA | 2841617 A1 | 1/2013 |
| CA | 2871305 A1 | 10/2013 |
| CA | 2915775 A1 | 10/2013 |

(56) References Cited

FOREIGN PATENT DOCUMENTS

| | | |
|---|---|---|
| CA | 2876018 A1 | 12/2013 |
| CA | 2895929 A1 | 6/2014 |
| CA | 2915070 A1 | 12/2014 |
| CN | 1035719 C | 8/1997 |
| CN | 1035720 C | 8/1997 |
| CN | 1035736 C | 8/1997 |
| CN | 101905155 A | 12/2010 |
| CN | 103650061 A | 3/2014 |
| EP | 2841607 B1 | 12/2016 |
| EP | 2748825 B1 | 3/2017 |
| GB | 1157117 A | 7/1969 |
| KR | 10-0936016 B | 1/2010 |
| KR | 10-1365797 B | 3/2014 |
| KR | 10-1370189 B | 3/2014 |
| KR | 10-1542708 B | 8/2015 |
| KR | 10-1587837 B | 1/2016 |
| KR | 10-1754430 B | 7/2017 |
| RU | 2403086 C2 | 11/2010 |
| RU | 2462793 C2 | 9/2012 |
| RU | 2560966 C2 | 8/2015 |
| RU | 2014147619 A | 6/2016 |
| RU | 2630475 C2 | 9/2017 |
| SU | 927753 A1 | 5/1982 |
| WO | WO 1992016949 A1 | 10/1992 |
| WO | WO 1994004463 A2 | 3/1994 |
| WO | WO 1994004463 A3 | 3/1994 |
| WO | WO 1995016996 A1 | 6/1995 |
| WO | WO 1997001852 A1 | 1/1997 |
| WO | WO 2000003399 A1 | 1/2000 |
| WO | WO 2007041730 A1 | 4/2007 |
| WO | WO 2009135163 A2 | 11/2009 |
| WO | WO 2009135163 A3 | 2/2010 |
| WO | WO 2007041730 A9 | 5/2010 |
| WO | WO 2010132043 A1 | 11/2010 |
| WO | WO 2011005736 A2 | 1/2011 |
| WO | WO 2011093938 A2 | 8/2011 |
| WO | WO 2011126522 A2 | 10/2011 |
| WO | WO 2011126522 A3 | 12/2011 |
| WO | WO 2011156446 A2 | 12/2011 |
| WO | WO 2011093938 A3 | 1/2012 |
| WO | WO 2012018752 A2 | 2/2012 |
| WO | WO 2012048077 A1 | 4/2012 |
| WO | WO 2011156446 A3 | 5/2012 |
| WO | WO 2012125994 A2 | 9/2012 |
| WO | WO 2013010047 A1 | 1/2013 |
| WO | WO 2017012655 A1 | 1/2013 |
| WO | WO 2013027207 A1 | 2/2013 |
| WO | WO 2012125994 A3 | 4/2013 |
| WO | WO 2012125994 A9 | 6/2013 |
| WO | WO 2013082699 A1 | 6/2013 |
| WO | WO 2013159201 A1 | 10/2013 |
| WO | WO 2013027207 A9 | 1/2014 |
| WO | WO 2014163956 A1 | 10/2014 |
| WO | WO 2014186898 A1 | 11/2014 |
| WO | WO 2016023112 A1 | 2/2016 |
| WO | WO 2016023113 A1 | 2/2016 |
| WO | WO 2016075212 A1 | 5/2016 |
| WO | WO 2016081484 A1 | 5/2016 |
| WO | WO 2016081675 A1 | 5/2016 |
| WO | WO 2016108939 A2 | 7/2016 |
| WO | WO 2016173664 A1 | 11/2016 |
| WO | WO 2016207054 A1 | 12/2016 |
| WO | WO 2017082748 A1 | 5/2017 |
| WO | WO 2018156828 A1 | 8/2018 |
| WO | WO 2018156835 A1 | 8/2018 |
| WO | WO 2018156910 A1 | 8/2018 |

OTHER PUBLICATIONS

J. V. Evans et al., "Zircomium Molybdate Gel as a Generator for Technetium-99mm—I. The Concept and its Evaluation." Appl. Radiat. Isot. vol. 38, No. 1, pp. 19-23 (1987).

P.W. Moore et al., "Zircomium Molybdate Gel as a Generator for Technetium-99mm—II. High Activity Generators." Appl. Radiat. Isot. vol. 38, No. 1, pp. 25-29 (1987).

Osso et al., "Preparation of a Gel of Zirconium Molybdate for Use in the Generators of. 99Mo-99mTc Prepared with 99Mo Produced by the 98Mo(n,g )99Mo Reaction," Presented at the 1998 International Meeting on Reduced Enrichment for Research and Test Reactors; Oct. 18-23, 1998; Sao Paulo, Brazil.

Monroy-Guzman et al., "Magnesium-Molybdate Compounds as a Matrix for 99Mo/99mTc Generators," Pharmaceuticals 2011, 4(2), 215-232.

Amin et al., "Effect of Al:Mo molar ratio on elution performance of 99Mo/99mTc generators based on Al99Mo gels," J Radioanal Nucl Chem (2016) 309;485-492.

Guedes-Silva et al., "Influence of Alumina Phases on the Molybdenum Adsorption Capacity and Chemical Stability for 99Mo/99mTc Generators Columns," Materials Research (2017); 19(4): 791-794.

Gopalakrishna et al., "Preparation of 99Mo from the 100Mo($\gamma$, $\eta$) reaction and chemical separation of 99mTc," J Radioanal Nucl Chem (2016) 308:431-438.

Fasih et al., "Preparation and evaluation of nano-crystalline titania as sorbent for 99Mo/99mTc generator," Separation and Science Technology (2016) 51:13, 2115-2121.

Pupillo et al., "Accelerator based production of 99Mo: a comparison between the 100Mo(p,x) and 96Zr($\alpha$,n) reactions," J Radioanal Nucl Chem (2015) 305:73-78.

Pupillo et al., "Experimental cross section evaluation for innovative 99Mo production via the ($\alpha$,n) reaction on 96Zr target," J Radioanal Nucl Chem (2014) 302:911-917.

El-Absy et al., "Preparation of 99Mo/99mTc generator based on alumina 99Mo-molybdate (VI) gel," J Radioanal Nucl Chem (2014) 299:1859-1864.

Iller et al., "Synthesis and structural investigations of gel metal oxide composites WO3—ZrO2, WO3—TO2, WO3—ZrO2—SiO2, and their evaluation as materials for the preparation of 188W/188Re generator," Applied Radiation and Isotopes 75 (2013) 115-127.

Chakravarty et al., "Nano Structured Metal Oxides as Potential Sorbents for 188W/188Re Generator: A Comparative Study," Separation Science and Technology (2013) 48:4, 607-616.

Chakravarty et al., :An electrochemical procedure to concentrate 99mTc availed from a zirconium- [99Mo] molybdate gel generator, Applied Radiation and Isotopes 70 (2012) 375-379.

Mostafa et al., "Labeling of ceftriaxone for infective inflammation imaging using 99mTc eluted from 99Mo 99mTc generator based on zirconium molybdate," Applied Radiation and Isotopes 68 (2010) 1959-1963.

Tereshatov et al., "Isocratic anion exchange separations of Group V elements," J Radioanal Nucl Chem (2010) 286:9-16.

Davarpanah et al., "Influence of drying conditions of zirconium molybdate gel on performance of 99mTc gel generator," Applied Radiation and Isotopes 67 (2009) 1796-1801.

Sahoo et al., "Synthesis, Characterization, and Photocatalytic Properties of ZrMo2O8," J. Phys. Chem. C 2009, 113, 10661-10666.

Sahoo et al., "Synthesis, structure and photocatalytic properties of β-ZrMo2O8," Bull. Mater. Sci., vol. 32, No. 3, Jun. 2009, pp. 337-342.

Magnaldo et al., "Nucleation and crystal growth of zirconium molybdate hydrate in nitric acid," Chemical Engineering Science 62 (2007) 766-774.

Monroy-Guzman et al., "Titanium Molybdate Gels as Matrix of 99Mo/99mTc Generators," Journal of Nuclear and Radiochemical Sciences, vol. 8, No. 1, pp. 11-19, 2007.

Monroy-Guzman et al., "Production optimization of 99Mo/99mTc zirconium molybate gel generators at semi-automatic device: DISIGEG," Applied Radiation and Isotopes 70 (2012) 103-111.

Monroy-Guzman et al., "99Mo/99mTc Generators Performances Prepared from Zirconium Molybate Gels," J. Braz. Chem. Soc., vol. 19, No. 3, 380-388, 2008.

Monroy-Guzman et al., "Determination of Mo, W and Zr in molybdates and tungstates of zirconium and titanium," Journal of Radioanalytical and Nuclear Chemistry, vol. 271, No. 3 (2007) 523-532.

Monroy-Guzman et al., "Effect of Zr:Mo ratio on 99mTc generator performance based on zirconium molybdate gels," Applied Radiation and Isotopes 59 (2003) 27-34.

(56) References Cited

OTHER PUBLICATIONS

International Search Report and Written Opinion of corresponding International Application PCT/US2018/019335, dated May 7, 2018.
International Search Report and Written Opinion of corresponding International Application PCT/US2018/019322, dated Jul. 11, 2018.
International Search Report and Written Opinion of corresponding International Application PCT/US2018/019443, dated Jul. 9, 2018.
Monroy-Guzman et al., "Titanium Molybdate Gels as Matrix of 99Mo/99mTc Generators", Journal of Nuclear and Radiochemical Sciences, vol. 8, No. 1 (Jan. 2007), p. 11-19 (p. 11, col. 1, para 1; p. 11, col. 2, para 4; p. 12; p. 13, col. 1, para 3; p. 13, col. 2, para 12; p. 14; p. 16, col. 1, para 3; p. 16, col. 2, para 1; p. 17, col. 2, para 1; p. 18, col. 1, para 2; p. 18, col. 2, para 1; abstract; title; tables 1-2; figure 2D, 3B and 4A.
Extended European Search Report, European Application No. 18758354.7, dated Nov. 25, 2020, 7 pages.
Extended European Search Report, European Application No. 18757129.4, dated Nov. 25, 2020, 6 pages.
Office Action from U.S. Appl. No. 15/902,534 dated Sep. 11, 2020.
Office Action and Search Report from Russian Patent Application No. 2019129820 dated Jun. 2, 2020.
Office Action and Search Report from Russian Patent Application No. 2019129825 dated Aug. 10, 2020.
Lidin R.A, et al., Khimicheskie svojstva neorganichheskikh veshchestv, Moscow, Kimia 1997, pp. 388, section 772, reaction 3. (not in English) (See Office Actions and Search Reports from Russian Patent Application Nos. 2019129820 and 2019129825).
Australian Examination Report from Australian Patent Application No. 2018224128 dated Feb. 24, 2020.
International Preliminary Report on Patentability, PCT/2018/019322, dated Aug. 27, 2019, 17 pages.
International Preliminary Report on Patentability, PCT/2018/019335, dated Aug. 27, 2019, 21 pages.
International Preliminary Report on Patentability, PCT/2018/019443, dated Aug. 27, 2019, 5 pages.

* cited by examiner

METAL-MOLYBDATE AND METHOD FOR MAKING THE SAME

CROSS-REFERENCE TO RELATED APPLICATIONS

This application claims priority from U.S. provisional patent application Ser. No. 62/463,020, filed on Feb. 24, 2017, in the United States Patent and Trademark Office and from U.S. provisional patent application Ser. No. 62/592,737, filed on Nov. 30, 2017, in the United States Patent and Trademark Office. The disclosures of which are incorporated herein by reference in their entireties.

TECHNICAL FIELD

The presently-disclosed invention relates generally to metal-molybdate materials suitable for use in technetium-99m generators (Mo-99/Tc-99m generators) and methods for making the same.

BACKGROUND OF THE INVENTION

Technetium-99m (Tc-99m) is the most commonly used radioisotope in nuclear medicine (e.g., medical diagnostic imaging). Tc-99m (m is metastable) is typically injected into a patient which, when used with certain equipment, is used to image the patient's internal organs. However, Tc-99m has a half-life of only six (6) hours. As such, readily available sources of Tc-99m are of particular interest and/or need in at least the nuclear medicine field.

Given the short half-life of Tc-99m, Tc-99m is typically obtained at the location and/or time of need (e.g., at a pharmacy, hospital, etc.) via a Mo-99/Tc-99m generator. Mo-99/Tc-99m generators are devices used to extract the metastable isotope of technetium (i.e., Tc-99m) from a source of decaying molybdenum-99 (Mo-99) by passing saline through the Mo-99 material. Mo-99 is unstable and decays with a 66-hour half-life to Tc-99m. Mo-99 is typically produced in a high-flux nuclear reactor from the irradiation of highly-enriched uranium targets (93% Uranium-235) and shipped to Mo-99/Tc-99m generator manufacturing sites. Mo-99/Tc-99m generators are then distributed from these centralized locations to hospitals and pharmacies through-out the country. Since the number of production sites are limited, and compounded by the limited number of available high flux nuclear reactors, the supply of Mo-99 is susceptible to frequent interruptions and shortages resulting in delayed nuclear medicine procedures.

There at least remains a need, therefore, for a process for producing material suitable for use in technetium-99m generators (Mo-99/Tc-99m generators).

SUMMARY OF INVENTION

One or more embodiments of the invention may address one or more of the aforementioned problems. Certain embodiments according to the invention provide a process for producing a metal-molybdate (also referred to herein as metal-Mo), such as a metal-Mo material suitable for use in technetium-99m generators. The term "metal-molybdate", as used herein, generally refers to either a metal-molybdate, metal-molybdenum, molybdenum-metalate, or any form of Mo-metal or metal-Mo species. Processes according to certain embodiments of the invention may comprise reacting a metal molybdenum (Mo) material in a liquid medium (e.g., an aqueous medium) with a first acid (e.g., a mineral acid) to provide a Mo composition and combining the Mo composition with a metal source to provide a metal-Mo composition. Processes according to certain embodiments of the invention may further comprise pH adjusting the metal-Mo composition with a base (e.g., ammonium hydroxide) to precipitate a plurality of metal-Mo particulates (also referred to herein interchangeably as particles). In accordance with certain embodiments of the invention, the metal-Mo particulates may be isolated from or separated from the liquid medium. In accordance with certain embodiments of the invention, the isolated metal-Mo particulates may take the form of a slurry including a residual amount of the liquid medium therein. The isolated metal-Mo particulates may be subjected to heat energy to at least partially dry the metal-Mo particulates. The metal-Mo particulates may be milled and washed. In accordance with certain embodiments of the invention, the processes may comprise irradiating a metal molybdenum target to provide the Mo material as discussed herein. That is, the step of irradiating a metal molybdenum target to provide the Mo material may be carried out prior to the combination of the metal Mo material in a liquid medium with the first acid. The metal molybdenum target, for example, may comprise a tubular capsule comprising metal molybdenum and a plurality of internal metal molybdenum components (e.g., balls, rods, wires, discs, etc.) housed inside of the tubular capsule. Alternatively, the metal molybdenum target, for example, may be one or more metal molybdenum components (e.g., balls, rods, wires, discs, etc.) used alone or in combination, such as a rod with a series of discs. In this regard, certain embodiments of the invention comprise a metal-Mo material produced according to processes disclosed herein.

In some embodiments of the invention, an intermediate product may be present for further processing if so desired.

In yet another aspect, the invention provides the metal-Mo material comprises a plurality metal-Mo particulates.

In accordance with certain embodiments of the invention, the process may comprise irradiating the resulting metal-Mo material comprising a plurality of metal-Mo particulates. For example, the irradiation may be carried out prior to loading the metal-Mo particulates into an elution vessel.

In accordance with certain embodiments of the invention, the metal-Mo material comprises an eluting efficiency of 30% or greater, an eluting efficiency of 80% or greater, 90% or greater, or 95% or greater. The metal-Mo material, in accordance with certain embodiments of the invention, may be disposed in an elution column (e.g., technetium-99m generator) and at least 90% (e.g., at least 95% or at least 99%) of a total technetium content releases from the metal-Mo material via passing an aqueous liquid (e.g., water, saline, dilute acid) through the metal-Mo material.

Other embodiments of the invention are described herein.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout, and wherein.

DETAILED DESCRIPTION

Figure 1:
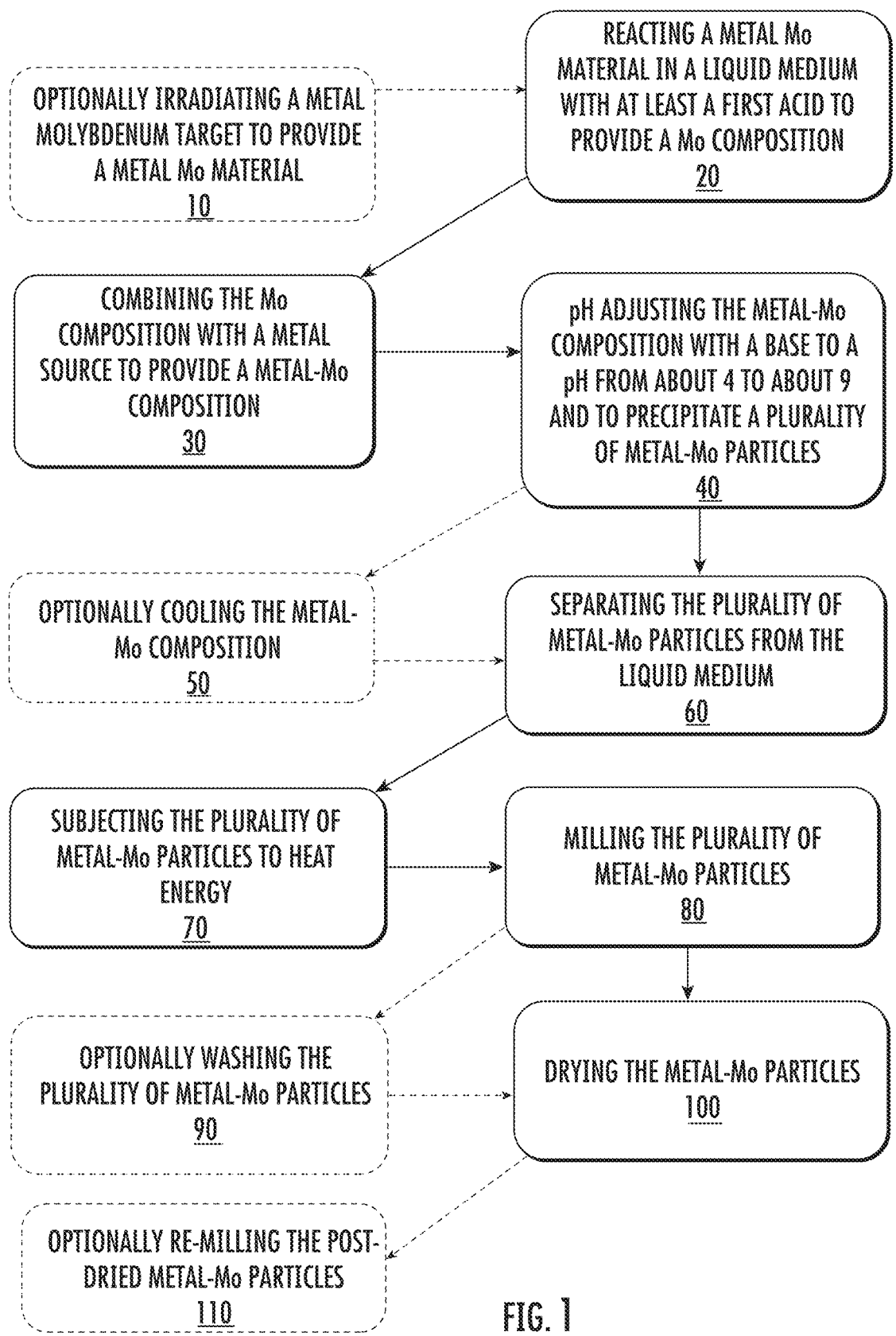
FIG. 1 is a block diagram of a process for producing a metal-molybdate material according to an embodiment of the invention.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The invention provides, according to certain embodiments, a process for producing a metal-molybdate (also referred to herein as metal-Mo), such as a metal-Mo material suitable for use in technetium-99m generators. The term "metal-molybdate", as used herein, generally refers to either a metal-molybdate, metal-molybdenum, molybdenum-metalate, or any form of Mo-metal or metal-Mo species.

In accordance with certain embodiments, the process may include a step of reacting a metal molybdenum (Mo) material (such as a solid molybdenum metal in a variety of forms including powder and bulk solids of various particle sizes and geometries) in a liquid medium with an acid or acids (e.g., a mineral acid) to provide a Mo composition (e.g., a solution of Mo) and combining the Mo composition with a metal source to provide a metal-Mo composition. Metal molybdenum, for example, is usually produced by powder metallurgy techniques in which Mo powder is hydrostatically compacted and sintered. A metal molybdenum material, in accordance with certain embodiments of the invention, may comprise Mo atoms, consist essentially of Mo atoms, or consist of Mo atoms. Non-limiting examples of a metal molybdenum material include, but are not limited to, natural Mo, enriched Mo (including, but not limited to, Mo enriched in Mo-98), Mo alloys (including, but not limited to, any material where the Mo content is above 50% and the other constituent(s) making the alloy is easily separated from the Mo via chemistry).

Processes according to certain embodiments of the invention may further comprise pH adjusting the metal-Mo composition with a base (e.g., ammonium hydroxide) to precipitate a plurality of metal-Mo particulates. In accordance with certain embodiments of the invention, the process for producing solid metal-Mo may comprise a single-pot process, in which the metal Mo material is transformed into solid metal-Mo particulates in a single pot (i.e., the same tank or pot).

In accordance with certain embodiments, the acid or acids utilized may comprise one or more mineral acids or hydrogen peroxide. In this regard, mineral acids suitable for combination with the metal Mo may comprise hydrochloric acid, nitric acid, sulfuric acid, phosphoric acid, hydrofluoric acid, boric acid, hydrobromic acid, perchloric acid, hydroiodic acid, halogen acids (such as HAt where At is Astatine), or any combination thereof. In accordance with certain embodiments, the mineral acid may comprise hydrochloric acid, nitric acid, or a combination thereof. In this regard, the metal Mo may be immersed in the liquid medium and agitated while one or more of the foregoing acids is added to lower the pH of the liquid medium. In accordance with certain embodiments, the step of reacting the metal molybdenum (Mo) material in the liquid medium with the first acid may subject the metal Mo material and/or a metal oxide formed thereby to a process including, but not limited to, oxidation, dissolution, other reaction processes, or a combination thereof.

In accordance with certain embodiments of the invention, the liquid medium may comprise an aqueous medium. In this regard, the liquid medium may comprise water. In accordance with certain embodiments of the invention, the liquid medium consists of water, to which the metal Mo and one or more of the foregoing acids are added.

In accordance with certain embodiments of the invention, the step of reacting the metal molybdenum (Mo) material in the liquid medium with the first acid may be performed at a molar ratio of Mo to acid (Mo:Acid) in a range of about of 0.1:1 to about 10:1.

The step of reacting the metal Mo may further comprise controlling a temperature of the liquid medium (e.g., aqueous medium), in which the metal Mo is immersed at any point during the reaction. In this regard, the temperature control of the liquid medium (e.g., aqueous medium) may comprise the addition of heat to the liquid medium, removal of heat from the liquid medium, no added heat, or a combination thereof. Addition and/or removal of heat may be achieved by a variety of known heat-transfer systems (e.g., internal tank coils, heat exchangers, jacketed tanks, etc.). In accordance with certain embodiments of the invention, for instance, the temperature of the liquid medium may be controlled throughout the reaction by adding and/or removing heat from the liquid medium as desired. In accordance with certain embodiments of the invention, for example, heat may be supplied to the liquid medium, in which the metal Mo is immersed, sufficient to raise the temperature of the liquid medium to or above about 25° C., to or above about 35° C., to or above about 45° C., to or above about 55° C., etc. The temperature of the liquid medium may begin to rise. In this regard, controlling the temperature of the liquid medium by removing heat given off may be desirable, for example, for at least safety concerns. If the liquid medium includes any co-chemicals, the boiling points of such chemicals may, at least partially, dictate the desired maximum temperature to which the liquid medium is allowed to reach. In accordance with certain embodiments of the invention, the temperature of the liquid medium may be controlled by maintaining the temperature of the liquid medium at or below about 80° C., for example, by removal of heat from the liquid medium. In accordance with certain embodiments of the invention, the temperature of the liquid medium may be controlled by maintaining the temperature of the liquid medium at or below about 100° C., at or below about 80° C., at or below about 70° C., at or below about 60° C., at or below about 50° C., at or below about 40° C.

Reacting may further comprise agitating the metal Mo material and the liquid medium during at least a portion of the step. In this regard, the agitation of the metal Mo material and liquid medium may provide an improved interaction of the metal Mo material with the liquid medium as the pH of the liquid medium is reduced via addition of acid (i.e., one or more mineral acids). For example, agitation may provide improved access of the metal Mo material to the acid in the liquid medium and may speed up any resulting reaction process including, but not limited to, oxidation, dissolution, or a combination thereof. In accordance with certain embodiments of the invention, for instance, the agitation may comprise mechanically mixing the metal Mo material and the liquid medium. In accordance with certain embodiments of the invention, the agitation may be improved by utilizing an internal tank baffles to facilitate vertical mixing of the metal Mo and liquid medium.

In accordance with certain embodiments of the invention, the step of combining the metal Mo material may comprise simultaneously, for at least a portion of the step, adding one or more acids to the liquid medium, in which the metal Mo material is immersed, controlling the temperature of the liquid medium, and agitating the metal Mo material and liquid medium. The resulting Mo composition (e.g., a solution of Mo) may then be subjected to further processing.

In accordance with certain embodiments of the invention, a process is provided for producing a metal-molybdate (Ti—Mo) comprising oxidizing a metal molybdenum (Mo) material, in whole or in part, in a liquid medium with a first acid to provide a Mo composition, combining the Mo composition with a metal source to provide a metal-Mo composition, and pH adjusting the metal-Mo composition with a base to precipitate a plurality of metal-Mo particulates.

In accordance with certain embodiments of the invention, a process is provided for producing a metal-molybdate (Ti—Mo) comprising dissolving a metal molybdenum (Mo) material, in whole or in part, in a liquid medium with a first acid to provide a Mo composition, combining the Mo composition with a metal source to provide a metal-Mo composition, and pH adjusting the metal-Mo composition with a base to precipitate a plurality of metal-Mo particulates.

The process parameters and/or process conditions for oxidizing and/or dissolving in the aforementioned embodiments can be the same as discussed herein as for the reacting step.

In accordance with certain embodiments of the invention, after formation of the Mo composition, the process may comprise combining the Mo composition with a metal source to provide a metal-Mo composition.

In accordance with embodiments of the invention, the metal source may comprise an element from the p-block, d-block, or f-block of the periodic table. The p-block of the periodic table includes elements from the six groups beginning with group 3A and ending with group 8A with the exception of helium. The p-block metals generally have high melting points and readily react with nonmetals to form ionic compounds. Metalloids have properties of metals and non-metals and are also in the p-block. The d-block of the periodic table includes elements from groups 3, 4, 5, 6, 7, 8, 9, 10, 11, and 12 of the periodic table. These elements are known as the transition metals. A transition metal (also called a transition element) can also be defined by the IUPAC definition that states that a transition metal is "an element whose atom has an incomplete d sub-shell, or which can give rise to cations with an incomplete d sub-shell." The f-block of the periodic table includes the lanthanide and actinide series. The f-block elements have one or more of their outermost electrons in the f-orbital but none in the d-orbital or p-orbital. The f-orbitals can contain up to seven pairs of electrons.

Non-limiting examples of metal sources are one or more metals, metalates, or metallic salts include, but are not limited to, elemental or unoxidized metal, metal oxide, metal hydroxide, metal halide, nitrate, phosphate, tetrefluoroboride, phosphorous hexafluoride, tosylate, acetate, formate, or any other counter anion capable of producing a soluble salt. This metal, metalate, or metallic salt can exist in various oxidation states $M^{n+}$, n=1, 2, 3, 4, 5, 6, and may be capable of forming an oxo-bridge or hydroxo-bridge with another metal, metalate, metallic salt, or molybdate. An oxo-bridge typically refers to an oxygen ion that covalently bonds to a metal in an M-O-M fashion.

In accordance with embodiments of the invention, the metal source is a metal, metalate, or metallic salt that achieves the following: (1) forms a discrete or complex unit, either a tetrahedral, octahedral, or more complex structure; (2) links with the discrete unit in which the $Mo_xO_y$ is present, wherein x is the number of Mo atoms and y is the number of O atoms; (3) persists under ionizing radiation without mutation and the bond formed with the $Mo_xO_y$ species remains; and/or (4) should the material be synthesized before irradiation of Mo, does not yield any daughter products from neutron bombardment that would be undesirable in the final eluate.

In the case of titanium, the titanium source may comprise a titanium chloride (e.g., $TiCl_3$). In accordance with certain embodiments of the invention, the titanium chloride may comprise titanium(III) chloride ($TiCl_3$), titanium(II) chloride ($TiCl_2$), titanium tetrachloride ($TiCl_4$), or any combination thereof.

In addition to the aforementioned titanium salts, a titanium salt existing in the $2^+$, $3^+$, or $4^+$ oxidation state may also be comprised of counter ions such as nitrates, $NO_3^-$, or other halides, $F^-$, $Br^-$, $At^-$, or $I^-$. Further titanium sources may include, but are not limited to, unoxidized titanium metal or metal carbonyl, or be combined in a variety of oxidation states with metal oxides, metal hydroxides, phosphates, tetrefluoroboride, phosphorous hexafluoride, tosylates, acetate, formate, or any other counter anion capable of producing a soluble salt.

In addition to titanium, other metals capable of forming an elutable structure with Mo can also be added in a variety of ratios. These metals may take the form of an unoxidized metal, or the aforementioned salt forms taken by titanium. In addition, these titanium metal substitutes may exist in a variety of oxidation states, $M^{n+}$, n=1, 2, 3, 4, 5, 6. Titanium substitutes will come from select p-block, d-block (transition metals), and/or f-block metals. Some of these metals may include, but are not limited to, Aluminum (Al) (p-block), Silicon (Si) (p-block), Tin (Sn) (p-block), Germanium (Ge) (p-block), Zirconium (Zr) (d-block), Hafnium (Hf) (d-block), Vanadium (V) (d-block), Chromium (Cr) (d-block), Manganese (Mn) (d-block), Cobalt (Co) (d-block), Nickel (Ni) (d-block), Iron (Fe) (d-block), Copper (Cu) (d-block), Niobium (Nb) (d-block), Rhodium (Rh) (d-block), Gadolinium (Gd) (f-block), Thorium (Th) (f-block), Cerium (f-block), Uranium (U) (f-block), Praseodymium (Pr) (f-block), or Terbium (Tb) (f-block).

The previously described metals may bond to the Mo unit in a variety of forms. In choosing a metal for an elutable structure, the metal preferably forms a direct covalent bond with the Mo unit. Bonding can occur through any method which will typically be oxo- and hydroxo-, bridges. The bonding form includes, but is not limited to, cyano, nitro, sulfide, nitride amido, acetate, carbonate, phosphate, and carbonyl bonding schemes or any combination of thereof as well as others typically found in inorganic compounds. The metal can bond with the Mo unit without precipitation or without forming its own discrete unit such as an oxide or salt resulting in a homogeneous or heterogeneous mixture of the molybdate unit and the metalate unit. It is preferable that the metal does not act as a binder to a Mo decay product or a Tc decay product.

The step of combining the Mo composition with the metal source to provide the metal-Mo composition, in accordance with certain embodiments of the invention, may comprise adding the metal source to the Mo composition. In accordance with certain embodiments of the invention, the Mo composition is agitated or mixed during addition of the metal source.

The addition of the metal source to the Mo composition may comprise, for example, dropwise addition of the metal source to the Mo composition. In this regard, the addition of the metal source to the Mo composition may comprise administering one drop (e.g., 0.05 mL) of the metal source at a time to an agitating Mo composition. In accordance with certain embodiments of the invention, the number of drops of the metal source added to the Mo composition per minute may vary. The step of combining the Mo composition with the metal source to provide the metal-Mo composition may also comprise adding an acid (e.g. a second mineral acid) to the Mo composition. In accordance with certain embodiments of the invention, the temperature may be dropped, preferably in a range of about 25° C. to about 35° C., when the metal source is added with the acid. The acid may comprise a mineral acid as disclosed above. For example, the mineral acid added to the Mo composition during the combination of the metal source and the Mo composition may comprise hydrochloric acid. In accordance with certain embodiments of the invention, the metal source and the acid (e.g., hydrochloric acid) may be simultaneously added to the Mo composition. For instance, the metal source may comprise a liquid composition including, for example, one or more metal-containing compounds disclosed herein (e.g., $TiCl_3$) and the acid (e.g., hydrochloric acid). In this regard, the addition of the metal source may comprise the simultaneous addition of metal-containing compound(s) and acid. In accordance with certain embodiments of the invention, the resulting metal-Mo composition may comprise a final pH of about 3 or less (e.g., about 2 or less, or about 1 or less) at the end of the step of combining the Mo composition with the metal source. In accordance with certain embodiments of the invention, in the case of titanium, the step of combining the Mo composition with a metal source (e.g., $TiCl_3$) to provide a metal-Mo composition may be performed until a molar ratio of titanium to Mo (metal:Mo) of about 0.1:1 to about 10:1 is reached.

Processes according to certain embodiments of the invention may further comprise pH adjusting the metal-Mo composition with a base to precipitate a plurality of metal-Mo particulates. A base suitable for neutralization of the acid digested salts or soluble salts include, but are not limited to, metal hydroxide(s) such as alkali and alkaline earth metal hydroxides, ammonium hydroxides, sodium hydroxide, quaternary alkyl amine hydroxides, or a combination thereof. In accordance with certain embodiments of the invention, the pH of the metal-Mo composition is adjusted with a base to a pH in the range from about 4 to about 9. As such, in certain embodiments of the invention, the pH of the metal-Mo composition may be adjusted to at least about any of the following: 4, 4.5, 5, 5.5, 6, 6.5, and 7 and/or at most about 9, 8.5, 8, 7.5, 7, 6.5, and 6. During the pH adjustment of the metal-Mo composition, the metal-Mo composition may be subjected to agitation, for example, to mechanical agitation.

In accordance with certain embodiments of the invention, the pH adjustment of the metal-Mo composition may comprise adding the base in a dropwise manner. In this regard, the addition of the base to the metal-Mo composition may comprise administering one drop (e.g., 0.05 mL) of the base at a time to an agitating metal-Mo composition. In accordance with certain embodiments of the invention, the number of drops of the base added to the metal-Mo composition per minute may vary. Other forms of administering the metal source can be used including, but not limited to, a mist, spray, or a combination thereof.

The metal-Mo composition after the pH adjustment step includes the plurality of precipitated metal-Mo particulates from the pH adjustment, and may be subjected to a cooling or chilling step either during pH adjustment and/or subsequent to the pH adjustment. In accordance with certain embodiments of the invention, the step of cooling the metal-Mo composition may comprise reducing the temperature of the metal-Mo composition to between about 0° C. to about 20° C. (e.g., about 3° C. to about 10° C.). As such, in certain embodiments of the invention, the step of cooling the metal-Mo composition may comprise reducing the temperature of the metal-Mo composition to at least about any of the following: 3° C., 5° C., 8° C., 10° C., and 12° C. and/or at most about 20° C., 15° C., 12° C., and 10° C.

Regardless of whether or not the metal-Mo composition after precipitation of the plurality of metal-Mo particulates is subjected to the cooling step discussed above, the metal-Mo composition may be subjected to a separating operation (e.g., a solid-liquid separation). In this regard, processes according to certain embodiments of the invention may comprise separating the plurality of metal-Mo particulates from the liquid medium (e.g., unwanted bulk liquid medium). In this regard, the metal-Mo particulates may be isolated from or separated from the unwanted liquid medium. In accordance with certain embodiments of the invention, the isolated metal-Mo particulates may take the form as slurry including a residual amount of the liquid medium therein. In accordance with certain embodiments of the invention, the step of separating the plurality of metal-Mo particulates from the liquid medium may comprising filtering (e.g., vacuum-filtering) or centrifuging the metal-Mo composition to retain at least most of the plurality of metal-Mo particulates. Filtering media may include, but are not limited to, paper, sintered metal, metal mesh, or a combination thereof. A primary and/or a secondary filtering media may be used. The separating step may comprise utilization of a metal filtering surface, wherein at least most of the plurality of metal-Mo particulates are retained on the metal filtering surface. As noted above, the isolated or retained metal-Mo particulates may take the form as a slurry including a residual amount of the liquid medium therein.

In accordance with certain embodiments of the invention, the isolated or retained metal-Mo particulates (e.g., in the form of a slurry) may be subjected to heat energy to at least partially dry the metal-Mo particulates. During exposure to heat energy, the residual liquid medium entrained in the metal-Mo particulates begins to evaporate. The metal-molybdate molecules, however, remain in a somewhat amorphous solid state without any strong crystal state.

The step of subjecting the plurality of metal-Mo particulates to heat energy, in accordance with certain embodiments of the invention, may comprise exposing the plurality of metal-Mo particulates to infrared radiation. In accordance with certain embodiments of the invention, the infrared radiation comprises a wavelength from about 700 nm to about 1400 nm. As such, in certain embodiments of the invention, the infrared radiation may comprise a wavelength from at least about any of the following: 700, 750, 800, 850, 900, 920, 940, 960, 980, and 1000 nm and/or at most about 1400, 1300, 1200, 1150, 1100, 1080, 1060, 1040, 1020, and 1000 nm.

In accordance with certain embodiments of the invention, the heat energy source may comprise convective heating, freeze drying, an infrared heater, such as one or more light-emitting-diodes (LEDs), quartz crystal, quartz infrared heating elements, and incandescent light bulbs producing infrared light. In accordance with certain embodiments of the invention, the operating temperature may be controlled to be from about 20° C. to about 80° C. In this regard, the operating temperature may comprise at least about any of the following: 20° C., 30° C., 40° C., 45° C., 50° C., 55° C., and 60° C. and/or at most about 80° C., 75° C., 70° C., 65° C., and 60° C.

Subsequent to subjecting the metal-Mo particulates to heat energy, the metal-Mo particulates may optionally be subjected to a milling or grinding operation. In accordance with certain embodiments of the invention, the metal-Mo particulates may be milled by many commercially available mills, such as ball mills, hammer mills, high pressure grinding mills, tower mills, and wet mills (e.g., conical wet mill).

In accordance with certain embodiments of the invention, the average size of the plurality of metal-Mo particulates after the milling step may comprise from about 10 microns to about 1275 microns (e.g., about 100 microns to about 200 microns, about 630 microns to about 1015 microns, etc.). In accordance with certain embodiments of the invention, for example, the average size of the plurality of metal-Mo particulates after the milling step may comprise from at least about any of the following: 10, 50, 75, 125, 150, 175, 200, 225, 250, 275, 300, 350, 400, 450, 500, 550, 600, 650, 700, 750, 800, 850, 900, 925, and 950 microns and/or at most about 1275, 1250, 1225, 1200, 1175, 1150, 1125, 1100, 1050, 1000, and 950 microns.

In accordance with certain embodiments of the invention, select particle sizes can be selected by mechanical filters, chemical filters, or a combination thereof.

The milled metal-Mo particulates, according to certain embodiments of the invention, may be subjected to a washing step.

In accordance with certain embodiments of the invention, the washed metal-Mo particulates may be collected and dried to remove most of the washing liquid. The drying operation is not particularly limited. After drying the post-washed metal-Mo particulates, the metal-Mo particulates may tend to agglomerate together. As such, the metal-Mo particulates may be subjected to a second milling process, in which the second milling process comprises a dry-milling process and the plurality of metal-Mo particulates after the second milling step may comprise from about 10 microns to about 1275 microns (e.g., about 100 microns to about 200 microns, about 630 microns to about 1015 microns, etc.). In accordance with certain embodiments of the invention, for example, the average size of the plurality of metal-Mo particulates after the second milling step may comprise from at least about any of the following: 10, 50, 75, 125, 150, 175, 200, 225, 250, 275, 300, 350, 400, 450, 500, 550, 600, 650, 700, 750, 800, 850, 900, 925, and 950 microns and/or at most about 1275, 1250, 1225, 1200, 1175, 1150, 1125, 1100, 1050, 1000, and 950 microns.

In accordance with certain embodiments of the invention, the processes may comprise irradiating a metal molybdenum target to provide the Mo material as discussed herein. The metal molybdenum target, for example, may comprise a tubular capsule comprising metal molybdenum and a plurality of internal metal molybdenum components (e.g., balls, rods, wires, discs, etc.) housed inside of the tubular capsule. For example, the tubular capsule may comprise a first end, a second end, and a wall connecting the first end and the second end to define a hollow cavity therein. In this regard, the plurality of internal metal molybdenum components (e.g., balls, rods, wires, discs, etc.) may be packed within the hollow cavity of the tubular capsule. In accordance with certain embodiments of the invention, at least the first end may be configured to allow access to the hollow cavity for loading and optionally unloading the plurality of internal metal molybdenum components (e.g., balls, rods, wires, discs, etc.). In this regard, at least the first end (or a portion thereon) may be configured to be removed from the tubular capsule to provide access to the hollow cavity. In accordance with certain embodiments of the invention, the metal Mo material in the reacting step comprises the plurality of internal metal molybdenum components, the tubular capsule, or both.

The metal molybdenum target may comprise a plurality of metal molybdenum discs (e.g., circular discs) that each comprise a length, a width, and a thickness in the z-direction. In this regard, the thickness may comprise a value that is less than both the length and width. In accordance with certain embodiments of the invention, the thickness comprises from about 2 microns to about 260 microns (e.g., from about 10 microns to about 150 microns). In accordance with certain embodiments of the invention, for example, the thickness comprise from at least about any of the following: 2, 10, 20, 30, 40, 50, 60, 70, 80, 90, and 100 microns and/or at most about 275, 260, 250, 225, 200, 175, 150, 140, 130, 120, 110, and 100 microns. In accordance with certain embodiments of the invention, the plurality of metal molybdenum discs are packed in a side-by-side relationship in the z-direction inside the tubular capsule. In accordance with certain embodiments of the invention, a plurality of metal molybdenum discs may be used without a capsule. In accordance with certain embodiments of the invention, the metal molybdenum discs may be formed from metal molybdenum sheets by, for example, a stamping process. In accordance with certain embodiments of the invention, the metal Mo material in the reacting step comprises the plurality of metal molybdenum discs, the tubular capsule component, or both.

FIG. 1 illustrates an example embodiment in accordance with the invention. In particular, FIG. 1 illustrates a process including an optional step (as indicated by the broken lines) of irradiating a metal molybdenum target to provide a metal Mo material at operation 10 prior to combination with the metal Mo material (e.g., received from operation 10 or alternatively received from a third party) in a liquid medium with at least a first acid to provide a Mo composition at operation 20. As illustrated in FIG. 1, the process includes a step of combining the Mo composition with a metal source to provide a metal-Mo composition at operation 30 and pH adjusting the metal-Mo composition with a base to a pH from about 4 to about 9 and to precipitate a plurality of metal-Mo particulates at operation 40. As illustrated in the example embodiment of FIG. 1, the metal-Mo composition may optionally be subjected to a step of cooling the metal-Mo composition at operation 50 prior to a step of separating the plurality of metal-Mo particulates from the liquid medium at operation 60. After operation 60, the isolated metal-Mo particulates can be subjected to a step of exposing the plurality of metal-Mo particulates to heat energy at operation 70 followed by a step of milling the plurality of metal-Mo particulates at operation 80. As illustrated by the particular example embodiment of FIG. 1, the process may then include an optional step of washing the plurality of metal-Mo particulates at operation 90 followed by a second drying step at operation 100. As shown in FIG. 1, the process may include an optional step 110 of re-milling (e.g., dry milling) the post-dried metal-Mo particulates.

As noted above, the metal molybdenum target that may be irradiated to provide the Mo material may comprise a tubular capsule and/or a plurality of metal molybdenum components (e.g., balls, rods, wires, discs, etc.).

The metal molybdenum target, according to certain embodiments of the invention, may be irradiated, for example, by neutron capture in a fission reactor. In accordance with certain embodiments of the invention, the Mo material as disclosed herein may be provided by a variety of Mo production technologies including, for example, fission reactors (e.g., reprocessed uranium, low-enriched uranium, and highly enriched uranium), particle accelerators, and neutron capture. In accordance with certain embodiments of the invention, the metal molybdenum target may be irradiated by any type of reactor in which the Mo target can be inserted. Non-limiting examples of reactors include, but are not limited to, High Flux Isotope Reactor (HFIR), a CANDU reactor (e.g., CANDU reactor, CANDU6 reactor, CANDU9 reactor, Advanced CANDU reactor (ACR), etc.). Other non-limiting examples of reactors are power reactors and research reactors including, but not limited to, University of Missouri Research Reactor (MURR), National Institute of Standards and Technology (NIST) Reactor, MIT Nuclear Research Reactor (MITR), and Advanced Test Reactor (ATR).

In this regard, the origin of the Mo material as disclosed herein is not particularly limited in accordance with certain embodiments of the invention.

In accordance with certain embodiments of the invention, for example, the average size of the plurality of metal-Mo particulates may comprise from at least about any of the following: 10, 50, 75, 100, 125, 150, 175, 200, 225, 250, 275, 300, 350, 400, 450, 500, 550, 600, 650, 700, 750, 800, 850, 900, 925, and 950 microns and/or at most about 1275, 1250, 1225, 1200, 1175, 1150, 1125, 1100, 1050, 1000, and 950 microns.

In accordance with certain embodiments of the invention, the metal-Mo material comprises an eluting efficiency of 30% or greater, an eluting efficiency of 80% or greater, 90% or greater, or 95% or greater. The metal-Mo material, in accordance with certain embodiments of the invention, may be disposed in an elution column to provide a technetium-99m generator and at least 90% (e.g., at least 95% or at least 99%) of a total technetium content releases from the metal-Mo material via passing an aqueous liquid (e.g., water, saline, dilute acid) through the metal-Mo material. In this regard, certain embodiments of the invention enable the use of larger elution columns (e.g., technetium-99m generators). For instance, the standard 20 milliliter saline eluting may extract technetium from elution columns much larger than the standard 3 milliliter elution column size. Accordingly, certain embodiments of the invention enable achievement of target Tc-99m activities from smaller than expected Mo activities. Consequently, reactors with lower fluxes may be used to provide commercially viable product to the industry and a greater number of reactors may participate in suitable Mo generation.

In this regard, certain embodiments of the invention enable use of elution columns (e.g., technetium-99m generators) exceeding the standard 3 milliliter size (e.g., 5 mL, 10 mL, 12 mL, 15 mL, 20 mL, 25 mL, 30 mL, 60 mL, or 100 mL) such that the use of reactors with smaller fluxes to produce the desired target technetium activity are now viable. For example, lower flux reactors that traditionally could not be utilized for generating a high enough specific activity of technetium for commercial purposes may now be viably utilized in accordance with certain embodiments of the invention. In this regard, a variety of reactors may be used to supply Mo to processes in accordance with certain embodiments of the invention.

As noted above, metal-Mo materials in accordance with certain embodiments of the invention enable the use of elution columns exceeding the standard 3 milliliter size (e.g., 5 mL, 10 mL, 12 mL, 15 mL, 20 mL, 25 mL, 30 mL, 60 mL, or 100 mL) such that the use of reactors with smaller fluxes to produce the desired target technetium activity are now viable.

Accordingly, the present invention also provides an elution pig configured to accept a variety of sizes of elution columns which will allow a variety of reactors (e.g. reactors of high flux and/or low flux) to be integrated into the supply chain for the production of Tc-99m. In accordance with certain embodiments of the invention, the elution pig may be configured to accept a variety of different sized elution columns including 3 mL, 5 mL, 10 mL, 12 mL, 15 mL, 20 mL, 25 mL, 30 mL, 60 mL, 100 mL or any combination thereof.

In accordance with certain embodiments of the invention, the metal-Mo particles may be irradiated prior to being loaded into a cask transfer case or an elution column. This step can eliminate the optional step of irradiating a metal molybdenum target at the front end of the process. Among the advantages of such a post-irradiation process step are that the chemical process can be performed without radiological control thereby reducing or eliminating radioactive waste generation, and that there is a decrease in processing time resulting in higher initial activity of the metal-Mo particles.

Figure 2:
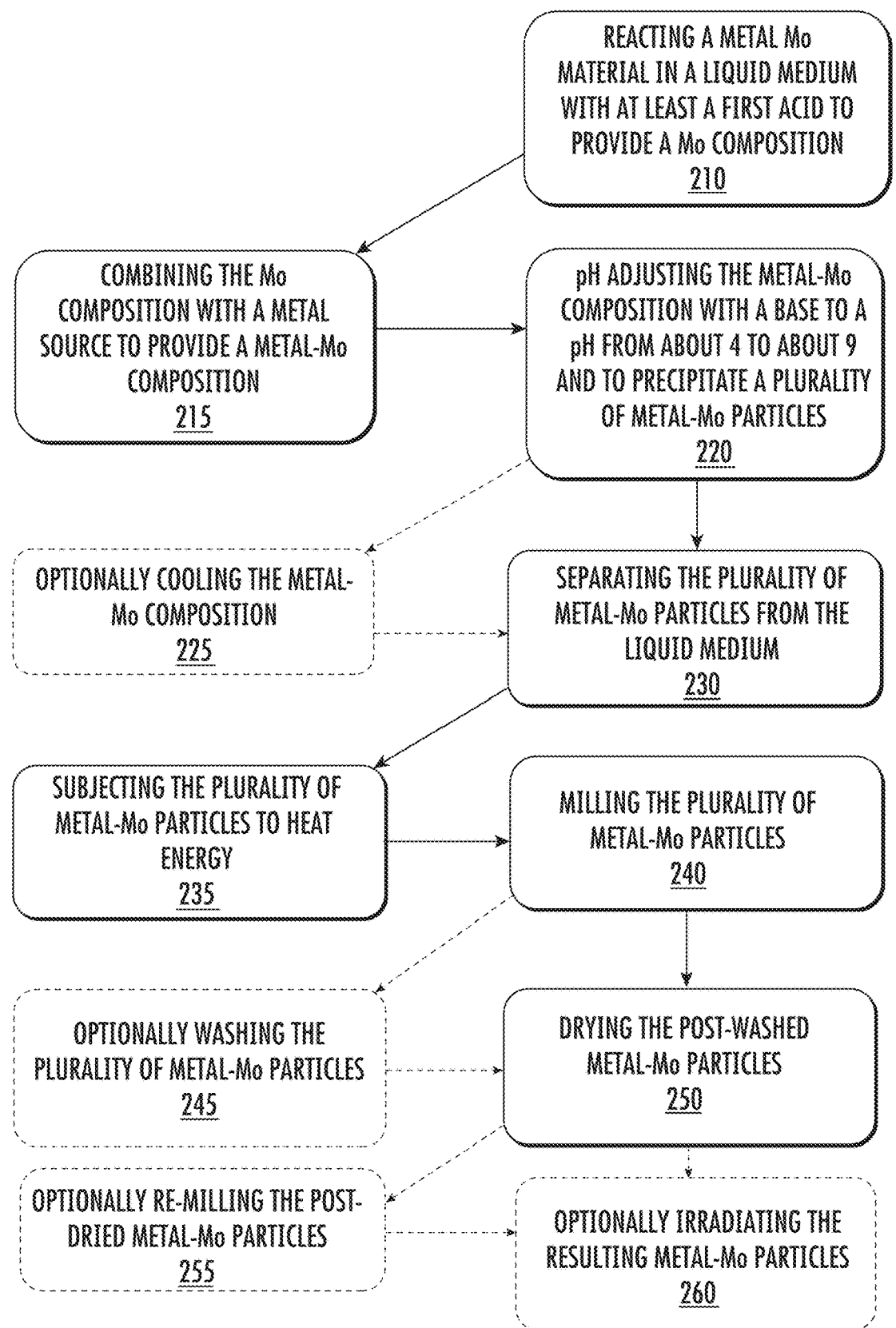
FIG. 2 is a block diagram of a process for producing a metal-molybdate material according to an embodiment of the invention with optional post-irradiation.

FIG. 2 illustrates this embodiment of post-irradiation in accordance with the invention. As illustrated in FIG. 2, the process includes step 210 of reacting a metal Mo material in a liquid medium with at least a first acid to provide a Mo composition. In step 215, the process includes combining the Mo composition with a metal source to provide a metal-Mo composition and pH adjusting the metal-Mo composition with a base to a pH from about 4 to about 9 and to precipitate a plurality of metal-Mo particles/particulates in step 220. As illustrated in the example embodiment of FIG. 2, the metal-Mo composition may optionally be subjected to step 225 of cooling the metal-Mo composition prior to step 230 of separating the plurality of metal-Mo particles from the liquid medium. After step 230, the isolated metal-Mo particles can be subjected to a step 235 of exposing the plurality of metal-Mo particles to heat energy followed by a step 240 of milling the plurality of metal-Mo particles. As illustrated by the particular example embodiment of FIG. 2, the process may then include an optional step 245 of washing the plurality of metal-Mo particles followed by a second drying step 250. As shown in FIG. 2, the process may include an optional step 255 of re-milling (e.g., dry milling) the post-dried metal-Mo particles. As illustrated by the particular example embodiment of FIG. 2, the process may then include an optional step 260 of irradiating the resulting metal-Mo particles prior to being loaded in an elution column.

Figure 3:
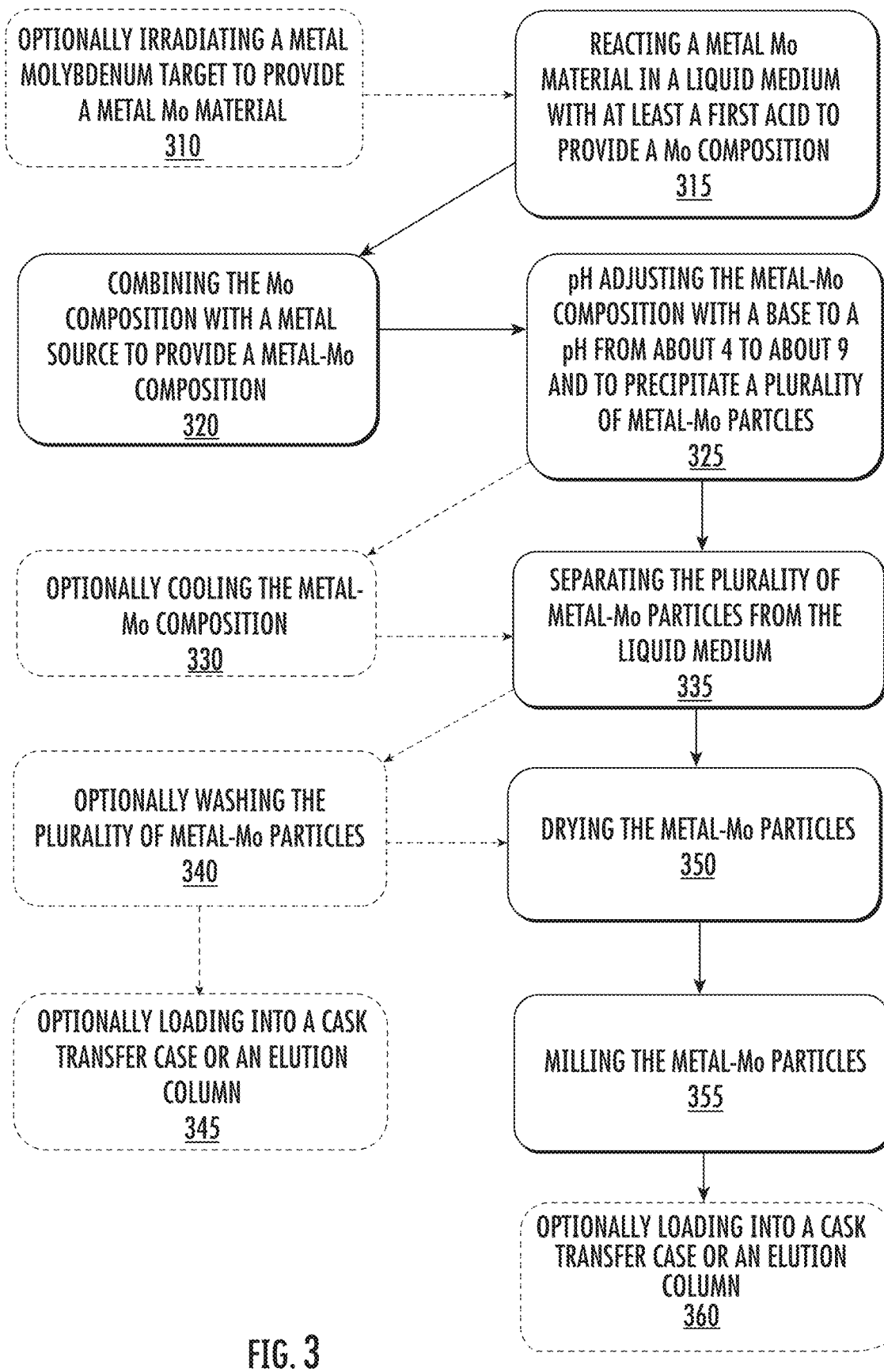
FIG. 3 is a block diagram of a process for producing a metal-molybdate material according to an embodiment of the invention.

In accordance with certain embodiments of the invention, another process for producing a metal-molybdate material is provided. As illustrated in FIG. 3, the process includes step 310 of optionally irradiating a metal molybdenum target to provide a metal Mo material. The process includes step 315 of reacting a metal Mo material in a liquid medium with at least a first acid to provide a Mo composition. In step 320, the process includes combining the Mo composition with a metal source to provide a metal-Mo composition and pH adjusting the metal-Mo composition with a base to a pH from about 4 to about 9 and to precipitate a plurality of metal-Mo particles or particulates in step 325. As illustrated in the example embodiment of FIG. 3, the metal-Mo composition may optionally be subjected to step 330 of cooling the metal-Mo composition prior to step 335 of separating the plurality of metal-Mo particles from the liquid medium. As illustrated by the particular example embodiment of FIG. 3, the process may then include an optional step 340 of washing the plurality of metal-Mo particles, preferably with deionized water. As shown in FIG. 3, the process may include an optional step 345 of optionally loading the metal-Mo particles as wet or in a slurry form into a cask transfer case or an elution column. If not subjected to step 345, the process includes a step 350 of drying the metal-Mo particles and a step 355 of milling the metal-Mo particles. As shown in step 360 of FIG. 3, the milled metal-Mo particles can be loaded into a cask transfer case or an elution column.

Figure 4:
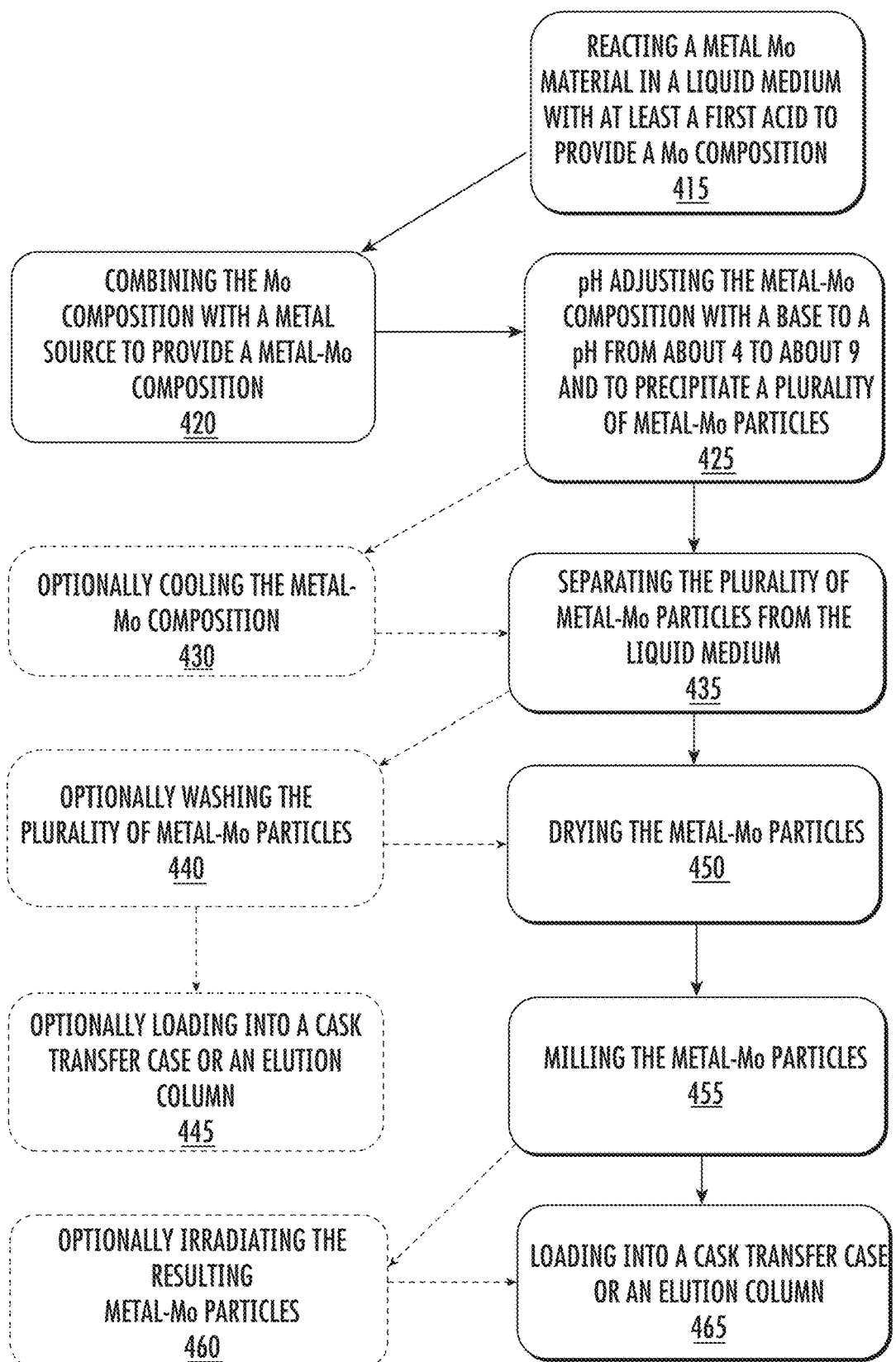
FIG. 4 is a block diagram of a process for producing a metal-molybdate material according to an embodiment of the invention with optional post-irradiation.

In accordance with certain embodiments of the invention, a process for producing a metal-molybdate material with an optional post-irradiation step is provided. FIG. 4 illustrates an example of another embodiment in accordance with the invention. As illustrated in FIG. 4, the process includes step 415 of reacting a metal Mo material in a liquid medium with at least a first acid to provide a Mo composition. In step 420, the process includes combining the Mo composition with a metal source to provide a metal-Mo composition and pH adjusting the metal-Mo composition with a base to a pH from about 4 to about 9 and to precipitate a plurality of metal-Mo particles or particulates in step 425. As illustrated in the example embodiment of FIG. 4, the metal-Mo composition may optionally be subjected to step 430 of cooling the metal-Mo composition prior to step 435 of separating the plurality of metal-Mo particles from the liquid medium. As illustrated by the particular example embodiment of FIG. 4, the process may then include an optional step 440 of washing the plurality of metal-Mo particles, preferably with deionized water. As shown in FIG. 4, the process may include an optional step 445 of optionally loading the metal-Mo particles as wet or in a slurry form into a cask transfer case or an elution column. If not subjected to step 445, the process includes a step 450 of drying the metal-Mo particles and a step 455 of milling the metal-Mo particles. As illustrated by the particular example embodiment of FIG. 4, the process may then include an optional step 460 of irradiating the resulting metal-Mo particles. As shown in step 465 of FIG. 4, the milled and optionally irradiated metal-Mo particles can be loaded into a cask transfer case or an elution column.

The processes of FIGS. 3 and 4 can be operated with various process parameters and still be within the scope of the present invention. However, examples of some processing parameters are set forth below for illustrative purposes only.

It is possible to use at a minimum, a concentration of 2 to 15 molar nitric acid in step 315 of FIG. 3 and in step 415 of FIG. 4, diluting with water as needed to achieve the required concentration. For the drying step as in step 350 of FIG. 3 or step 450 of FIG. 4, for example, the drying temperature may range from 70° C. to 200° C. In the processes of FIGS. 3 and 4, for example, the initial charge of molybdenum can be low such as 20 grams. Similarly, the volume of the metal source can also be low, for example, such as 134 mL for a 20 gram charge of Mo. The amount of ammonium hydroxide will change as a consequence of the lower amount of the metal source. The particle size preferably can vary from 10 microns (μm) to 250 microns (μm) in diameter.

Figure 5:
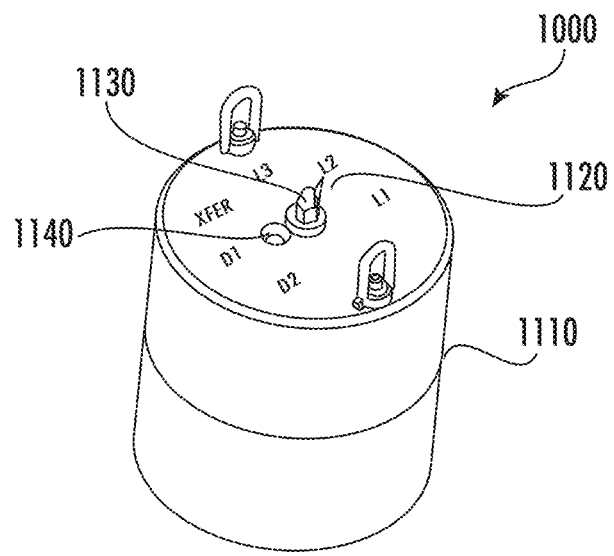
FIG. 5 illustrates a cask transfer case according to one embodiment of the invention.
Figure 6:
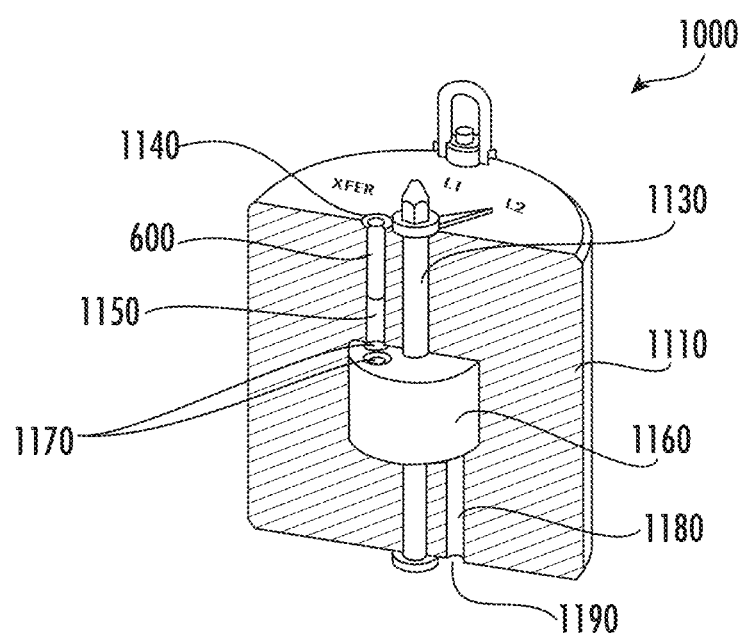
FIG. 6 illustrates a cross-sectional view of the cask transfer case illustrated in FIG. 5.

In yet another aspect, the present invention provides a cask transfer case and process. In order to move the highly radioactive Mo material from the reactor to the location for chemical processing (e.g., addition to metal source, etc.) or to move the irradiated metal-Mo particles, certain embodiments of the invention provide a cask transfer case that may shield personnel from undesirable doses of radioactivity. The cask transfer case may also allow for safe loading of the Mo material and transfer of the Mo material as well as unloading of the Mo material. FIG. 5, for instance, illustrates an example embodiment of a cask transfer case 1000 including a housing (e.g., including lead) 1110 and a dial 1120 attached to a rotating shaft 1130 that extends at least partially through the body of the housing. As showing in FIG. 5, the dial 1120 may be rotated to indicate an operating condition of the cask transfer case 1000. As shown in FIG. 5, for example, "L1" indicates that the cask transfer case is in an operating condition for loading a radioactive material into a first location, as discussed in greater detail below, via material inlet port 1140. As shown in FIG. 5, the cask transfer case 1000 includes a plurality of loading locations (e.g., "L1", L2", and "L3"). For instance, FIG. 6 is a cross-sectional view of FIG. 5 and illustrates the internal configuration of a cask transfer case 1000 according to certain embodiments of the invention. As shown in FIG. 6, the material inlet port 1140 is operatively connected to inlet conduit 1150. FIG. 6, for instance, illustrates an inlet port 1140 for radioactive Mo material 600 to be inserted through and into the inlet conduit 1150. As shown in FIG. 6, the rotating shaft 1130 is attached to an internal conduit housing 1160 that defines one or more internal conduits 1170 defined by the internal conduit housing. In this regard, the one or more internal conduits 1170 extend throughout the entire length of the internal conduit housing 1160. In this regard, the length of the one or more internal conduits 1170 comprise a length greater than a length of material (e.g., radioactive Mo material 600) loaded therein such that the internal conduit housing may be freely rotated about the axis of the rotating shaft 1130. In accordance with certain embodiments of the invention, one of the internal conduits 1170 may be aligned with the inlet conduit 1150 when the dial 1120 is positioned to indicate loading of a material. As such, a material (e.g., radioactive Mo material 600) to be loaded into the cask transfer case 1000 may be inserted through the inlet port 1140 and travel through the inlet conduit 1150 and rest inside an aligned internal conduit 1170 (e.g., the bottom of the loaded material may rest on an underlying internal portion of the housing 1110 and confined by the internal conduit 1170). As shown in FIG. 6, the housing 1110 also includes an exit conduit 1180 located underneath the internal conduit housing 1160 such that a material loaded in the cask transfer case may be dropped or released from the internal conduit 1170 when the dial is positioned to indicate an operation condition of dropping material (e.g., "D1", D2", and "D3" of FIG. 5). In such an operating condition, an internal conduit 1170 may be aligned with the exit conduit 1180 such that the loaded material drops out of the internal conduit, passes through the exit conduit, and exits the cask transfer case 100 through exit port 1190. As illustrated by FIG. 5, the cask transfer case may comprise an operating condition indicating the cask transfer case is ready for being transferred (e.g., "XFER" in FIG. 5) or relocated without risk of any material loaded therein from exiting through either the inlet port 1140 or the exit port 1190. For example, when the cask transfer cask 1000 is in the transfer operating condition according to certain embodiments of the invention, none of the internal conduits 1170 are aligned with the inlet conduit 1150 or the exit conduit 1180. That is, the inlet conduit 1150 is note aligned with any of the internal conduits 1170 and/or the exit conduit 1180 is not aligned with any of the internal conduits 1170. In this regard, the cask transfer cask 1000 would be safe to relocated to transfer radioactive material disposed therein.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A process for producing a metal-molybdate (metal-Mo), comprising:
    reacting a metal molybdenum (Mo) material in a liquid medium with a first acid to provide a Mo composition, wherein the liquid medium comprises an aqueous medium;
    combining the Mo composition with a metal source to provide a metal-Mo composition; and
    pH adjusting the metal-Mo composition with a base to precipitate a plurality of metal-Mo particulates,
    controlling a temperature of the aqueous medium via addition of heat to the aqueous medium, removal of heat from the aqueous medium, or both, and
    agitating the metal Mo material and the aqueous medium during at least a portion of the reaction,
    wherein the metal source comprises a metal, a metalate, or a metallic salt, and
    the metal, the metalate, or the metallic salt forms a bond with another metal, metalate, metallic salt, or molybdate, and
wherein the bond comprises a cyano, nitro, sulfide, nitride amido, acetate, carbonate, phosphate, carbonyl, or a combination thereof.

2. The process of claim 1, wherein the first acid comprises a mineral acid.

3. The process of claim 2, wherein the mineral acid is a halogen acid.

4. The process of claim 3, wherein the halogen acid is selected from the group consisting of hydrochloric acid, hydrofluoric acid, hydrobromic acid, hydroiodic acid, and a combination thereof.

5. The process of claim 3, wherein the mineral acid is selected from the group consisting of hydrochloric acid, nitric acid, sulfuric acid, and a combination thereof.

6. The process of claim 1, wherein reacting the metal Mo material in the liquid medium with the first acid is performed at a molar ratio of the Mo material to the first acid in a range of about 0.1:1 to about 10:1.

7. The process of claim 1, wherein reacting the metal Mo material in the liquid medium with the first acid subjects the metal Mo material to oxidation, dissolution, or a combination of oxidation and dissolution.

8. The process of claim 1, wherein reacting the metal Mo material in the liquid medium with the first acid subjects a metal oxide formed from the combination to oxidation, dissolution, or a combination of oxidation and dissolution.

9. The process of claim 1, wherein controlling the temperature of the aqueous medium comprises heating the aqueous medium above 25° C.

10. The process of claim 1, wherein controlling the temperature of the aqueous medium comprises maintaining the temperature of the aqueous medium below about 80° C.

11. The process of claim 1, wherein controlling the temperature of the aqueous medium comprises maintaining the temperature of the aqueous medium below about 70° C.

12. The process of claim 1, wherein controlling the temperature of the aqueous medium comprises maintaining the temperature of the aqueous medium below about 60° C.

13. The process of claim 1, wherein controlling the temperature of the aqueous medium comprises maintaining the temperature of the aqueous medium below about 50° C.

14. The process of claim 1, wherein controlling the temperature of the aqueous medium comprising maintain the temperature of the aqueous medium below about 40° C.

15. The process of claim 1, wherein agitating comprises mechanically mixing the metal Mo material and the aqueous medium.

16. The process of claim 1, wherein the metal source comprises an element from a p-block, d-block, or f-block of periodic table.

17. The process of claim 1, wherein the metal source is selected from the group consisting of elemental or unoxidized metal, metal oxide, metal hydroxide, metal halide, nitrate, phosphate, tetrefluoroboride, phosphorous hexafluoride, tosylate, acetate, formate, any other counter anion capable of producing a soluble salt, and a combination thereof.

18. The process of claim 1, wherein the metal, metalate, or metallic salt exists in various oxidation states of $M^{n+}$, where n=1, 2, 3, 4, 5, or 6.

19. The process of claim 1, wherein the bond comprises an oxo-bridge, a hydroxo-bridge, or a combination thereof.

20. The process of claim 1, wherein the metal, metalate or metallic salt forms a discrete structural unit or a complex structural unit.

21. The process of claim 1, wherein the metal, metalate, or metallic salt links with a discrete structural unit in which $Mo_xO_y$ is present, and x is a number of Mo atoms and y is a number of O atoms.

22. The process of claim 1, wherein the metal, metalate, or metallic salt persists under ionizing radiation without mutation and the bond formed with $Mo_xO_y$ remains, and x is a number of Mo atoms and y is a number of O atoms.

23. The process of claim 1, wherein the metal, metalate, or metallic salt does not yield any daughter products from neutron bombardment that are undesirable in the final eluate.

24. The process of claim 1, wherein the metal source is selected from the group consisting of Aluminum, Silicon, Tin, Germanium, Zirconium, Titanium, Hafnium, Vanadium, Chromium, Manganese, Cobalt, Nickel, Iron, Copper, Niobium, Rhodium, Gadolinium, Thorium, Cerium, Uranium, Praseodymium, Terbium, and a combination thereof.

25. The process of claim 24, wherein the titanium is a titanium salt selected from the group consisting of titanium (III) chloride (TiCl$_3$), titanium(II) chloride (TiCl$_2$), titanium tetrachloride (TiCl$_4$), and a combination thereof.

26. The process of claim 25, wherein the titanium salt comprises a counter ion selected from the group consisting of nitrates, halides, and a combination thereof.

27. The process of claim 1, wherein combining the Mo composition with the metal source is performed until a molar ratio of titanium to Mo of about 0.1:1 to about 10:1 is reached.

28. The process of claim 1, wherein combining the Mo composition with the metal source to provide the metal-Mo composition further comprises adding a second acid to the Mo composition.

29. The process of claim 28, wherein the second acid comprises a mineral acid.

30. The process of claim 28, wherein the second acid comprises hydrochloric acid.

31. The process of claim 28, wherein adding the second acid occurs simultaneously with adding the metal source to the Mo composition.

32. The process of claim 1, wherein the metal-Mo composition comprises a final pH of about 3 or less at an end of the step of combining the Mo composition with the metal source.

33. The process of claim 1, wherein pH adjusting the metal-Mo composition comprises adding the base to provide a pH in the range from about 4 to about 9.

34. The process of claim 1, wherein the base for pH adjusting the metal-Mo composition comprises ammonium hydroxide.

35. The process of claim 1, wherein pH adjusting the metal-Mo composition comprises adding the base to the metal-Mo composition dropwise.

36. The process of claim 1, further comprising cooling the metal-Mo composition during the step of pH adjusting the metal-Mo composition, subsequent to the step of pH adjusting the metal-Mo composition, or both.

37. The process of claim 36, wherein cooling the metal-Mo composition comprises reducing the temperature of the metal-Mo composition from between about 0° C. to about 20° C.

38. The process of claim 36, wherein cooling the metal-Mo-99 composition comprises reducing the temperature of the metal-Mo composition from between about 3° C. to about 10° C.

39. The process of claim 1, further comprising separating the plurality of metal particulates from the liquid medium.

40. The process of claim 39, wherein separating the plurality of metal-Mo particulates from the liquid medium comprises filtering the metal-Mo composition to retain at least most of the plurality of metal-Mo particulates.

41. The process of claim 40, wherein filtering the metal-Mo composition comprises utilization of a metal filtering surface.

42. The process of claim 41, wherein at least most of the plurality of metal-Mo particulates are retained on the metal filtering surface.

43. The process of claim 39, wherein the metal-Mo composition comprises a temperature from between about 0° C. to about 20° C. during the step of separating the plurality of metal-Mo particulates from the liquid medium.

44. The process of claim 1, further comprising milling the plurality of metal-Mo particulates.

45. The process of claim 44, wherein milling comprises wet milling.

46. The process of claim 44, wherein the average size of the plurality of metal-Mo particulates after milling is in a range of from about 10 microns to about 1275 microns.

47. The process of claim 44, wherein the average size of the plurality of metal-Mo particulates after milling is in a range of from about 10 microns to about 1015 microns.

48. The process of claim 1, further comprising washing the plurality of metal-Mo particulates with water.

49. The process of claim 1, further comprising drying the plurality of metal-Mo particulates.

50. The process of claim 1, further comprising irradiating the plurality of metal-Mo particulates.

51. The process of claim 1, further comprising irradiating a metal molybdenum target to provide the metal Mo material.

52. The process of claim 51, wherein the metal molybdenum target comprises a plurality of metal molybdenum discs.

53. The process of claim 51, wherein metal Mo material comprises the plurality of metal molybdenum discs, a tubular capsule component, or both.

54. A process for producing a metal-molybdate (metal-Mo), comprising:
reacting a metal molybdenum (Mo) material in a liquid medium with a first acid to provide a Mo composition;
combining the Mo composition with a metal source to provide a metal-Mo composition; and
pH adjusting the metal-Mo composition with a base to precipitate a plurality of metal-Mo particulates,
wherein the metal source is titanium, and wherein the titanium comprises unoxidized titanium metal or metal carbonyl.

55. The process of claim 54, wherein the titanium is combined with a metal oxide, metal hydroxide, phosphate, tetrefluoroboride, phosphorous hexafluoride, tosylate, acetate, formate, or any other counter anion capable of producing a soluble salt.

56. The process of claim 54, wherein combining the Mo composition with the metal source to provide the metal-Mo composition comprises adding the metal source to the Mo composition.

57. The process of claim 56, wherein adding the metal source to the Mo composition comprises addition of the metal source to the Mo composition in a form selected from the group consisting of a drop, spray, mist, and an combination thereof.

58. A process for producing a metal-molybdate (metal-Mo), comprising:
oxidizing, in whole or in part, a metal molybdenum (Mo) material in a liquid medium with a first acid to provide a Mo composition;
combining the Mo composition with a metal source to provide a metal-Mo composition; and
pH adjusting the metal-Mo composition with a base to precipitate a plurality of metal-Mo particulates,
wherein the metal source is titanium and wherein the titanium comprises unoxidized titanium metal or metal carbonyl.

59. A process for producing a metal-molybdate (metal-Mo), comprising:
dissolving, in whole or in part, a metal molybdenum (Mo) material in a liquid medium with a first acid to provide a Mo composition;
combining the Mo composition with a metal source to provide a metal-Mo composition; and pH adjusting the metal-Mo composition with a base to precipitate a plurality of metal-Mo particulates, wherein the metal source is titanium and wherein the titanium comprises unoxidized titanium metal or metal carbonyl.

60. A process for producing a metal-molybdate (metal-Mo), comprising:

combining a metal molybdenum (Mo) material in a liquid medium with a first acid to provide a Mo composition;

combining the Mo composition with a metal source to provide a metal-Mo composition; and pH adjusting the metal-Mo composition with a base to precipitate a plurality of metal-Mo particulates, wherein the metal source is titanium and wherein the titanium comprises unoxidized titanium metal or metal carbonyl.

* * * * *

UNITED STATES PATENT AND TRADEMARK OFFICE
CERTIFICATE OF CORRECTION

PATENT NO. : 11,286,172 B2
APPLICATION NO. : 15/902140
DATED : March 29, 2022
INVENTOR(S) : William Earl Russell, II et al.

It is certified that error appears in the above-identified patent and that said Letters Patent is hereby corrected as shown below:

On the Title Page

On the Page 3, in Column 1, under "Other Publications", Line 1, delete ""Zircomium" and insert -- "Zirconium --.

On the Page 3, in Column 1, under "Other Publications", Line 4, delete ""Zircomium" and insert -- "Zirconium --.

On the Page 3, in Column 2, under "Other Publications", Line 3, delete "(n,g )" and insert -- (n,g) --.

On the Page 3, in Column 2, under "Other Publications", Line 32, delete "TO2," and insert -- $TiO_2$, --.

On the Page 3, in Column 2, under "Other Publications", Line 62, delete "molybate" and insert -- molybdate --.

On the Page 3, in Column 2, under "Other Publications", Line 65, delete "Molybate" and insert -- Molybdate --.

In the Specification

In Column 2, Line 36, after "plurality" insert -- of --.

In Column 6, Lines 7-8, delete "tetrefluoroboride" and insert -- tetrafluoroboride --.

In Column 6, Line 41, delete "tetrefluoroboride" and insert -- tetrafluoroboride --.

In Column 14, Line 35, delete "L2"," and insert -- "L2", --.

In Column 14, Line 67, delete "D2"," and insert -- "D2", --.

Signed and Sealed this
Thirty-first Day of January, 2023

*Katherine Kelly Vidal*

Katherine Kelly Vidal
*Director of the United States Patent and Trademark Office*

CERTIFICATE OF CORRECTION (continued)
U.S. Pat. No. 11,286,172 B2

In the Claims

In Column 15, Line 65, in Claim 5, delete "claim 3," and insert -- claim 2, --.

In Column 16, Line 41, in Claim 17, delete "tetrefluoroboride" and insert -- tetrafluoroboride --.

In Column 18, Line 41, in Claim 55, delete "tetrefluoroboride" and insert -- tetrafluoroboride --.